United States Patent [19]

Praefcke et al.

[11] Patent Number: 4,758,373
[45] Date of Patent: Jul. 19, 1988

[54] CARBOCYCLIC COMPOUNDS

[75] Inventors: Klaus Praefcke; Bernd Kohne, both of Berlin; Eike Poetsch, Mühltal, all of Fed. Rep. of Germany

[73] Assignee: Merck Patent Gesellschaft mit beschrankter Haftung, Darmstadt, Fed. Rep. of Germany

[21] Appl. No.: 843,406

[22] Filed: Mar. 24, 1986

[30] Foreign Application Priority Data

Mar. 22, 1985 [DE] Fed. Rep. of Germany ....... 3510325

[51] Int. Cl.⁴ .................. G02F 1/13; C09K 19/06; C09K 19/34; C09K 19/32; C09K 19/30; C09K 19/20
[52] U.S. Cl. .................. 252/299.6; 252/299.61; 252/299.62; 252/299.63; 252/299.64; 252/299.65; 252/299.66; 252/299.67; 252/299.68; 252/299.5; 350/350 R
[58] Field of Search ............. 252/299.6, 299.5, 299.62, 252/299.61, 299.63, 299.66, 299.67, 299.65, 299.64, 299.68; 350/350 R, 350 S

[56] References Cited

U.S. PATENT DOCUMENTS

| 3,311,664 | 3/1967 | Reifschneider | 252/299.6 |
| 3,557,130 | 1/1971 | Petersson | 546/318 |
| 4,163,006 | 7/1979 | Spivack | 252/299.6 |
| 4,333,709 | 6/1982 | Dubois et al. | 252/299.62 |
| 4,430,650 | 2/1984 | Billard et al. | 252/299.62 |
| 4,578,210 | 3/1986 | Praefcke et al. | 252/299.63 |
| 4,631,143 | 12/1986 | Praefcke et al. | 252/299.62 |
| 4,702,562 | 10/1987 | Scheuble et al. | 252/299.63 |
| 4,713,196 | 12/1987 | Praefcke et al. | 252/299.63 |

FOREIGN PATENT DOCUMENTS

| 3334056 | 4/1985 | Fed. Rep. of Germany | 252/299.01 |
| 219020 | 2/1985 | German Democratic Rep. | 252/299.6 |

OTHER PUBLICATIONS

Kok, D. M., et al. Abstracts of the Tenth International Liq. Cryst. Conf., H9, presented 15–21 Jul. 1984, York, U.K.
Takenaka, S. et al., Mol. Cryst. Liq. Cryst., vol. 111, pp. 227–236 (1984).
Tinh, N., et al., Liquid Crystals & Ordered Fluids, vol. 4, pp. 1123–1130 (1984) Plenum Press., N.Y.
Chandrasekhar, S., Mol. Cryst., Liq. Cryst. vol. 63, pp. 171–180 (1981).
MacNicol, D., et al., J.C.S. Chem. Comm., pp. 494–495(1976).
Gilmore, C. J., et al., Tetrahedron Letters, vol. 24, No. 31, pp. 3269–3272 (1983).
MacNicol, D. D., et al., Tetrahedron Letters, vol. 23, No. 40, pp. 4131–4134 (1982).
Kok, D. M. et al., Mol. Cryst. Liq. Cryst. vol. 129, pp. 53–60 (Jul. 1985).

Primary Examiner—Teddy S. Gron
Attorney, Agent, or Firm—Millen & White

[57] ABSTRACT

Carbocyclic compounds of the formula I

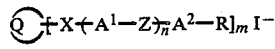

wherein
Q is a benzene or cyclohexane ring or a naphthalene system,
X is in each case $-CH_2-(CH_2)_p-$ wherein it is also possible for one or two non-adjacent $CH_2$ groups to be replaced by $-O-$, $-S-$, $-CO-$, $-O-CO-$, $-CO-O-$ or $-CH=CH-$,
p is 0, 1 or 2,
$A^1$ and $A^2$ independently of one another are each a 1,4-phenylene group which is unsubstituted or monosubstituted or polysubstituted by halogen atoms and/or $CH_3$ groups and/or CN groups and in which it would also be possible for one or more CH groups to be replaced by N atoms, a 1,4-cyclohexylene group wherein it would also be possible for one or two non-adjacent $CH_2$ groups to be replaced by $-O-$ and/or $-S-$, a piperidine-1,4-diyl group or a 1,4-bicyclo[2.2.2]octylene group,
Z is $-CO-O-$, $-O-CO-$, $-O-$, $-CH_2-$, $-CH_2O-$, $-OCH_2-$, $-CH_2CH_2-$, $-CHCN-CH_2-$, $-CH_2-CHCN-$, $-CH=CH-$, $-CH=N-$, $-N=CH-$, $-NO=N-$, $-N=NO-$ or a single bond,
n is 0, 1 or 2 and
R is alkyl having 1 to 20 C atoms wherein it would also be possible for one or more non-adjacent $CH_2$ groups to be replaced by $-O-$, $-CO-$, $-O-CO-$, $-CO-O-$ or $-CH=CH-$, H, F, Cl, Br, I, OH, $NH_2$, COOH or CN, m being 6 in the event that Q=benzene or cyclohexane and being 8 in the event that Q=naphthalene, subject to the proviso that, in the event that X=$-OCH_2-$ and $-(A^1-Z)_n-A^2-R$=p-alkoxyphenyl, Q is a cyclohexane ring, are suitable for use as components of discotic, liquid-crystal phases.

19 Claims, No Drawings

CARBOCYCLIC COMPOUNDS

BACKGROUND OF THE INVENTION

Cyclic compounds, namely hexalkanoyloxybenzenes, are known (cf. S. Chandrasekhar, *Mol. Cryst. Liq. Cryst.*, 63, (1981), 171-179 and the literature indicated therein).

Other compounds having discotic properties and their use are described for example, in U.S. Pat. No. 4,333,709.

SUMMARY OF THE INVENTION

It is an object of the invention to fine new, stable, liquid-crystal or mesogenic compounds suitable for use as components of discotic, liquid-crystal phases.

Upon further study of the specification and appended claims, further objects and advantages of this invention will become apparent to those skilled in the art.

This object has been achieved by providing the compounds of the formula:

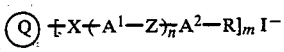

wherein

Q is a benzene or cyclohexane ring or a naphthalene system,

X is in each case —$CH_2$—$(CH_2)_p$— wherein it is also possible for one or two non-adjacent $CH_2$ groups to be replaced by —O—, —S—, —CO—, —O—CO—, —CO—O— or —CH=CH—, p is 0, 1 or 2, $A^1$ and $A^2$ independently of one another are each a 1,4-phenylene group which is unsubstituted or monosubstituted or polysubstituted by halogen atoms and/or $CH_3$ groups and/or CN groups and in which it is also possible for one or more CH groups to be replaced by N atoms, a 1,4-cyclohexylene group wherein it is also possible for one or two non-adjacent $CH_2$ groups to be replaced by —O— and/or —S—, a piperidine-1,4-diyl group or a 1,4-bicyclo[2.2.2]octylene group, Z is —CO—O—, —O—CO—, —O—, —$CH_2$—, —$CH_2O$—, —$OCH_2$—, —$CH_2CH_2$—, —CHCN—$CH_2$—, —$CH_2$—CHCN—, —CH=CH—, —CH=N—, —N=CH—, —NO=N—, —N=NO— or a single bond, n is 0, 1 or 2 and R is alkyl having 1 to 20C atoms wherein it is also possible for one or more non-adjacent $CH_2$ groups to be replaced by —O—, —CO—, —O—CO—, —CO—O— or —CH=CH—, H, F, Cl, Br, I, OH, $NH_2$, COOH or CN, m being 6 in the event that Q=benzene or cyclohexane and being 8 in the event that Q=naphthalene, subject to the proviso that, in the event that X=—$OCH_2$— and —($A^1$—Z)$_n$—$A^2$—R=p-alkoxyphenyl, Q is a cyclohexane ring.

DETAILED DISCUSSION

In the following text, for the sake of simplicity, Bz is a benzene nucleus having six free valences, Ch is a cyclohexane-1,2,3,4,5,6-hexayl group, Np is a naphthalene system having eight free valences, Phe is a 1,4-phenylene group, Cy is a 1,4-cyclohexylene group, Dio is a 1,3-dioxane-2,5-diyl group, Dit is a 1,3-dithiane-2,5-diyl group, Bi is a bicyclo[2.2.2]octylene group, Pip is a piperidine-1,4-diyl group, Pyn is a pyridyl group and Pyr is a pyrimidine-2,5-diyl group, it being possible for the disubstituted groups, in particular the 1,4-phenylene group, to be unsubstituted or substituted by one or two F and/or Cl atoms and/or $CH_3$ groups and/or CN groups.

The compounds of the formula I can be used like similar compounds as components of discotic, liquid-crystal phases, in particular for displays based on the guest-host effect, the effect of the deformation of aligned phases, the effect of dynamic scattering or a change in the elliptisization of light.

It has been found that the compounds of the formula I are excellently suitable for use as components of discotic, liquid-crystal phases. In particular, it is possible with their aid to prepare stable, discotic, liquid-crystal phases having a temperature range of the meso-phase which is broad and advantageously situated for electro-optical effects.

The compounds of the formula I are also suitable for use as an anisotropic, discotic matrix for spectroscopic investigations. See also U.S. Pat. No. 4,333,709.

Surprisingly, the compounds of the formula I prove to be discotic, liquid-crystal compounds having in some cases very broad meso-ranges.

In addition, the provision of the compounds of the formula I broadens considerably, in a very general way, the range of liquid-crystal substances which are suitable from various aspects of technical performance for the preparation of discotic mixtures.

The compounds of the formula I are also suitable for use as intermediate products for the preparation of other substances which can be used as constituents of liquid-crystal, discotic phases.

In the pure state, the compounds of the formula I are colorless and they form liquid-crystal meso-phases within a temperature range which is advantageously situated for electrooptical use. They are very stable to chemicals, heat and light.

The invention therefore relates to the compounds of the formula I and to a process for the preparation of compounds of the formula I, according to claim 1, characterized in that, in order to prepare ethers of the formula I wherein at least one of the radicals X is —$CH_2$—$(CH_2)_p$— wherein one or two non-adjacent $CH_2$ groups have been replaced by —O—, a corresponding hydroxy compound is etherified, and/or in order to prepare thioethers of the formula I wherein at least one of the radicals X is —$CH_2$—$(CH_2)_p$— wherein one or two non-adjacent $CH_2$ groups have been replaced by —S—, a corresponding halogen compound is reacted with a corresponding thiol or a salt of the latter, and/or in order to prepare compounds of the formula I wherein at least one of the radicals X is —$CH_2$—$(CH_2)_p$—, a compound which otherwise corresponds to the formula I but contains one or more reducible group(s) and/or C—C bond(s) instead of H atoms is treated with a reducing agent.

The invention also relates to the use of the compounds of the formula I as components of discotic, liquid-crystal phases. The invention also relates to discotic, liquid-crystal phases containing at least one compound of the formula I and to liquid-crystal display elements containing phases of this type.

In the preceding and following text Q, X, $A^1$, Z, $A^2$, R, m and n have the meaning indicated, unless anything to the contrary is expressly noted.

The compounds of the formula I accordingly embrace benzene derivatives of the partial formula Ia, cyclohexane derivatives of the partial formula Ib and naphthalene derivatives of the partial formula Ic:

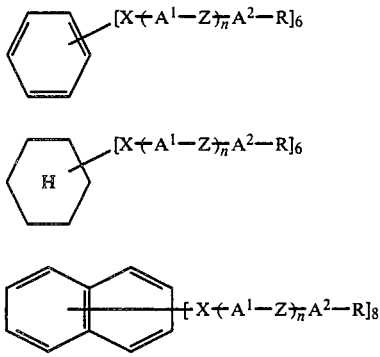

Ia

Ib

Ic

Preferred compounds of the formula I are those wherein Q is a cyclohexane ring.

Preferred compounds of the formula I are those in which the radicals $—X—(A^1—Z)_nA^2—R$ are identical and correspond to the following partial formulae I1 to I24:

| | |
|---|---|
| $Ch[—O—CO—(A^1—Z)_n—A^2—R]_6$ | I1 |
| $Ch[—CO—O—(A^1—Z)_n—A^2—R]_6$ | I2 |
| $Ch[—O—CH_2—(A^1—Z)_n—A^2R]_6$ | I3 |
| $Ch[—CH_2—O—(A^1—Z)_n—A^2—R]_6$ | I4 |
| $Ch[—CH_2CH_2—(A^1—Z)_n—A^2—R]_6$ | I5 |
| $Ch[—OCH_2CH_2—(A^1—Z)_n—A^2—R]_6$ | I6 |
| $Ch[—CH_2CH_2CH_2—(A^1—Z)_n—A^2—R]_6$ | I7 |
| $Ch[—SCH_2—(A^1—Z)_n—A^2—R]_6$ | I8 |
| $Bz[—O—CO—(A^1—Z)_n—A^2—R]_6$ | I9 |
| $Bz[—CO—O—(A^1—Z)_n—A^2—R]_6$ | I10 |
| $Bz[—O—CH_2—(A^1—Z)_n—A^2R]_6$ | I11 |
| $Bz[—CH_2—O—(A^1—Z)_n—A^2—R]_6$ | I12 |
| $Bz[—CH_2CH_2—(A^1—Z)_n—A^2—R]_6$ | I13 |
| $Bz[—OCH_2CH_2—(A^1—Z)_n—A^2—R]_6$ | I14 |
| $Bz[—CH_2CH_2CH_2—(A^1—Z)_n—A^2—R]_6$ | I15 |
| $Bz[—SCH_2—(A^1—Z)_n—A^2—R]_6$ | I16 |
| $Np[—O—CO—(A^1—Z)_n—A^2—R]_8$ | I17 |
| $Np[—CO—O—(A^1—Z)_n—A^2—R]_8$ | I18 |
| $Np[—O—CH_2—(A^1—Z)_n—A^2R]_8$ | I19 |
| $Np[—CH_2CH_2—(A^1—Z)_n—A^2—R]_8$ | I21 |
| $Np[—OCH_2CH_2—(A^1—Z)_n—A^2—R]_8$ | I22 |
| $Np[—CH_2CH_2CH_2—(A^1—Z)_n—A^2—R]_8$ | I23 |
| $Np[—SCH_2—(A^1—Z)_n—A^2—R]_8$ | I24 |

The compounds of the formulae I1, I2, I3, I5, I6, I9, I16, I17 and I24 are preferred.

Moreover, of the cyclohexanes of the formula Ib and L1 to I8, those in which the substituents opposite to each other are situated equatorially and in the trans-position relative to one another are preferred. This corresponds to the configuration of scyllo-inositol.

Compounds of the formula I containing one or more asymmetric C atoms can exist in a racemic or optically active form, both forms being embraced by formula I. R is preferably alkyl, —Oalkyl, —CO—O—alkyl, —O—CO—alkyl, —CO—alkyl, —CH₂—CH=CH—alkyl(-trans), —CH₂CH₂—CH=CH—alkyl—(trans), F, OH, COOH or CN, particularly preferably alkyl, —Oalkyl or —CO—O—alkyl, alkyl being in each case an alkyl radical in which it is also possible for a non-terminal (oxaalkyl) group or two non-adjacent (dioxaalkyl) CH₂ groups to be replaced by O atoms. These radicals can be linear or branched. Preferably, they are linear and have 3, 4, 5, 6, 7, 8, 9, 10, 11, 12 or 13C atoms and, accordingly, are preferably propyl, butyl, pentyl, hexyl, heptyl, octyl, nonyl, decyl, undecyl, dodecyl, tridecyl, 2-oxapropyl (=methoxymethyl), 2-oxabutyl (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, and also ethyl, tetradecyl, pentadecyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 2-, 3-, 4-, 5-, 6-, 7-, 8-, 9- or 10-oxaundecyl, 2-, 3-, 4-, 5-, 6-, 7-, 8-, 9-, 10- or 11-oxadodecyl, 2-, 3-, 4-, 5-, 6-, 7-, 8-, 9-, 10-, 11- or 12-oxatridecyl, 2,4-dioxapentyl, 2,4-, 2,5- or 3,5-dioxahexyl or 2,4-, 2,5-, 2,6-, 3,5-, 3,6- or 4,6-dioxaheptyl.

Compounds of the formula I having branched groups can have improved solubility in the customary liquid-crystal base materials, and are particularly important as chiral doping substances, if they are optically active. Branched groups of this type as a rule contain not more than one chain branching. Preferred branched alkyl radicals are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-oxa-3-methylbutyl and 3-oxa-4-methylpentyl.

Among the compounds of the formula I and the partial formulae, preferred compounds are those in which the radical R has one of the preferred meanings indicated.

X is preferably —CH₂—(CH₂)$_p$— wherein it is also possible for a CH₂ group to be replaced by —O— or —O—CO—. p is preferably 0 or 1. Particularly preferred meanings for X are indicated below: —O—CO—, —O—CH₂—, —O—CH₂CH₂—, —CH₂—CH₂—, —CH₂—CH₂—CH₂—, —CO—O— and —CH₂—O—.

—O—CO— and —CH₂—CH₂— are particularly preferred.

A¹ and A² independently of one another are each preferably Cy, Phe, Dio, Dit, Bi, Pip, Pyn, Pyr or PhX, particularly preferably Cy, Phe or Pyn.

PhX is a 1,4-phenylene group which is substituted in the 2-position or 3-position by F, Cl, CN or CH₃, especially F or CN.

Cy is preferably a trans-1,4-cyclohexylene group which is unsubstituted or substituted in the 1-position Or 4-position, in an axial position, by CN.

n is preferably 0 or 1, particularly preferably 0.

Z is preferably —CO—O—, —O—CO—, —CH₂O—, —OCH₂—, —CH₂CH₂— or a single bond.

A polysubstituted 1,4-phenylene group is preferably disubstituted in 2- and 3-position. Halogen is preferably fluorine. R is preferably alkyl or alkyl wherein it is possible for one or two (preferably in α- and ω-position) CH₂ groups to be replaced by —O—, —CO—, —O—CO—, —CO—O— or —CH=CH—.

The following are particularly preferred meanings of —(A¹—Z)ₙ—A²—:

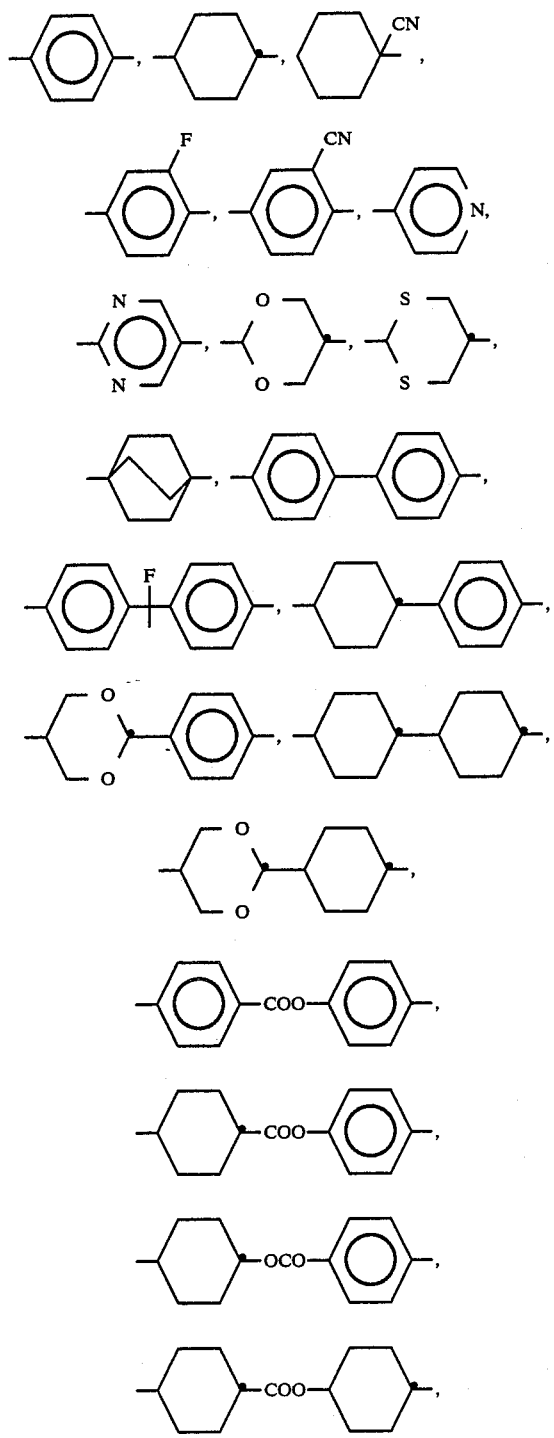

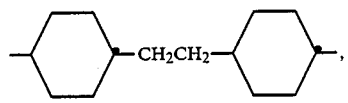

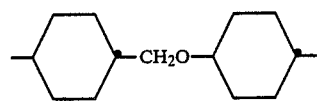

The compounds of the formula I are prepared by methods which are in themselves known, such as are described in the literature (for example in the standard works, such as Houben-Weyl, Methoden der Organischen Chemie (Methods of Organic Chemistry), Georg-Thieme-Verlag, Stuttgart), specifically under reaction conditions which are known and suitable for the reactions mentioned. In this connection it is also possible to make use of variants which are in themselves known but are not mentioned here in detail.

The starting materials are either known or can be prepared without difficulty analogously to known compounds by methods which are in themselves known. They can, if desired, also be formed in situ in such a way that they are not isolated from the reaction mixture, but are immediately reacted further to give the compounds of the formula I.

Ethers of the formula I can be obtained by etherifying corresponding hydroxy compounds, it being preferable first to convert the hydroxy compound into a corresponding metal derivative, for example into the corresponding alkali metal alcoholate or alkali metal phenate by treatment with NaH, NaNH₂, NaOH, KOH, Na₂CO₃ or K₂CO₃. This metal derivative can then be reacted with the corresponding alkyl halide or sulfonate or dialkyl sulfate, preferably in an inert solvent, such as acetone, 1,2-dimethoxyethane, dimethylformamide (DMF) or dimethyl sulfoxide or an excess of aqueous or aqueous-alcoholic NaOH or KOH at temperatures between about 20° and 100°.

Esters of the formula I can be obtained by esterifying corresponding carboxylic acids with corresponding alcohols.

Instead of the carboxylic acids and/or the alcohols, it is also possible to use reactive derivatives thereof.

Suitable reactive derivatives of the carboxylic acids mentioned are especially the acid halides, in particular the chlorides and bromides, and also the anhydrides, for example also mixed anhydrides, azides or esters, in particular alkyl esters having 1–4C atoms in the alkyl group.

Suitable reactive derivatives of the alcohols mentioned are, in particular, the corresponding metal alcoholates wherein OM group(s) replace the OH group(s) and wherein M is an equivalent of a metal, preferably an alkali metal, such as Na or K.

The esterification is advantageously carried out in the presence of an inert solvent. Very suitable solvents are, in particular, ethers, such as diethyl ether, di-n-butyl ether, THF, dioxane or anisole, ketones, such as acetone, butanone or cyclohexanone, amides, such as DMF or phosphoric acid hexamethyltriamide, hydrocarbons, such as benzene, toluene or xylene, halogenated hydrocarbons, such as carbon tetrachloride or tetrachloroethylene, sulfoxides, such as dimethyl sulfoxide, or sulfolane and carboxylic acids, such as trifluoroacetic acid.

Water-immiscible solvents can at the same time be used with advantage for the removal by azeotropic distillation of the water formed in the esterification. Occasionally it is also possible to use an excess of an organic base, for example pyridine, quinoline or triethylamine, as the solvent for the esterification. The esterification can also be carried out in the absence of a solvent, for example by merely heating the components in the presence of sodium acetate. The reaction temperature is usually between $-50°$ and $+250°$, preferably between $-20°$ and $+80°$. At these temperatures the esterification reactions are usually complete after 15 minutes to 48 hours.

In detail, the reaction conditions for the esterification depend largely on the nature of the starting materials used. Thus a free carboxylic acid is, as a rule, reacted with a free alcohol in the presence of a strong acid, for example a mineral acid, such as hydrochloric acid or sulfuric acid. A preferred mode of reaction is to react an acid anhydride or, in particular, an acid chloride with an alcohol, preferably in a basic medium, bases of importance being, in particular, alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. A further preferred embodiment of the esterification consists in first converting the alcohol into the sodium alcoholate or potassium alcoholate, for example by treatment with ethanolic sodium hydroxide solution or potassium hydroxide solution, isolating this alcoholate and suspending it, together with sodium bicarbonate or potassium carbonate, in acetone or diethyl ether by stirring, and adding a solution of the acid chloride or anhydride in diethyl ether, acetone or DMF to this suspension, preferably at temperatures between about $-25°$ and $+20°$.

Thioethers of the formula I can be prepared by reacting a corresponding halogen compound, preferably a bromine or chlorine compound, such as hexachlorobenzene or hexachlorocyclohexane, with a corresponding thiol or—preferably—a salt of the latter, in particular the corresponding Na thiolate. This reaction can be carried out in the presence or absence of an inert solvent, specifically at temperatures between about $-20°$ and $250°$, preferably between $10°$ and $150°$. Examples of suitable solvents are hydrocarbons, such as benzene, toluene, xylenes or mesitylene; tertiary bases, such as triethylamine, pyridine or picolines; alcohols, such as methanol, ethanol or butanol; glycols and glycol ethers, such as ethylene glycol, diethylene glycol or 2-methoxyethanol; ketones, such as acetone; ethers, such as tetrahydrofuran or dioxane; amides, such as DMF or phosphoric acid hexamethyltriamide (HMPT); and sulfoxides, such as dimethyl sulfoxide. Mixtures of these solvents are also suitable.

The compounds of the formula I wherein X is $-CH_2-(CH_2)_p-$ can be prepared by reducing a compound which otherwise corresponds to the formula I, but contains one or more reducible group(s) and/or C—C bond(s) instead of H atoms.

Suitable reducible groups are preferably C—C double bonds or carbonyl groups, in particular keto groups, and also, for example, free or esterified hydroxyl groups or halogen atoms attached to aromatic nuclei. Preferred starting materials for the reduction correspond to the formula I, but can contain a $-CH=CH-$ group instead of a $-CH_2CH_2-$ group and/or a $-CO-$ group instead of a $-CH_2-$ group and/or a free or functionally modified OH group (for example an OH group in the form of its p-toluenesulfonate) instead of an H atom.

The reduction can be carried out, for example, by catalytic hydrogenation at temperatures between about $0°$ and about $200°$ and pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are preferably noble metals, such as Pt or Pd, which can be employed in the form of oxides (for example $PtO_2$ or PdO), on a carrier (for example Pd on charcoal, calcium carbonate or strontium carbonate) or in a finely divided form.

Ketones can also be reduced by the methods of Clemmensen (using zinc, amalgamated zinc or tin and hydrochloric acid, preferably in aqueous alcoholic solution or in a heterogeneous phase using water/toluene, at temperatures between about $80°$ and $120°$) or Wolff-Kishner (using hydrazine, preferably in the presence of an alkali, such as KOH or NaOH, in a high-boiling solvent, such as diethylene glycol or triethylene glycol, at temperatures between about $100°$ and $200°$) to give the corresponding compounds of the formula I containing alkyl groups and/or $-CH_2CH_2-$ bridges.

Reductions by means of complex hydrides are also possible. For example, arylsulfonyloxy groups can be removed reductively by means of $LiAlH_4$, in particular p-toluenesulfonyloxymethyl groups can be reduced to methyl groups, preferably in an inert solvent, such as diethyl ether or THF, at temperatures between about $0°$ and $100°$. Double bonds can be hydrogenated (even in the presence of CN groups!) by means of $NaBH_4$ or tributyl tin hydride in methanol; thus, for example, the corresponding cyclohexane derivatives are formed from 1-cyanocyclohexene derivatives.

The discotic, liquid-crystal phases according to the invention comprise 2 to 15, preferably 3 to 12, components, including at least one compound of the formula I. The other constituents are preferably selected from the known discotic, liquid-crystal substances, in particular from the classes of hexa-substituted benzene or triphenylene derivatives. The phases according to the invention contain about 0.1 to 100%, preferably 10 to 100%, of one or more compounds of the formula I.

The preparation of the discotic, liquid-crystal phases according to the invention is carried out in a manner which is in itself customary. As a rule, the components are dissolved in one another, preferably at an elevated temperature.

The discotic, liquid-crystal phases according to the invention can also be modified by means of suitable additives. For example, it is possible to add conductive salts for improving the conductivity, pleochroic dyestuffs or substances for modifying the dielectric anisotropy, the viscosity and/or the orientation of the discotic phases.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

"Customary working up" means as follows: water is added, the mixture is extracted with methylene chloride, the phases are separated, the organic phase is dried and evaporated and the product is purified by crystallization and/or chromatography.

EXAMPLE 1

A mixture of 1. g of scyllo-inositol, 70 mmol of trans-4-nonylcyclohexanecarboxylic acid chloride and 20 ml of trifluoroacetic acid is stirred at room temperature for 15 hours and then at 50° for 2 hours. Customary working up (extraction with chloroform and flash column chromatography using 2:1 petroleum ether/chloroform) gives hexakis-(trans-4-n-nonylcyclohexylcarbonyl)-scyllo-inositol, m.p. 89°, c.p. 273°.

The following are obtained analogously using the corresponding acid chlorides:
hexakis-(trans-4-methylcyclohexylcarbonyl)-scyllo-inositol
hexakis-(trans-4-ethylcyclohexylcarbonyl)-scyllo-inositol
hexakis-(trans-4-propylcyclohexylcarbonyl)-scyllo-inositol
hexakis-(trans-4-butylcyclohexylcarbonyl)-scyllo-inositol
hexakis-(trans-4-pentylcyclohexylcarbonyl)-scyllo-inositol
hexakis-(trans-4-hexylcyclohexylcarbonyl)-scyllo-inositol
hexakis-(trans-4-heptylcyclohexylcarbonyl)-scyllo-inositol
hexakis-(trans-4-octylcyclohexylcarbonyl)-scyllo-inositol
hexakis-(trans-4-decylcyclohexylcarbonyl)-scyllo-inositol
hexakis-(trans-4-undecylcyclohexylcarbonyl)-scyllo-inositol
hexakis-(trans-4-dodecylcyclohexylcarbonyl)-scyllo-inositol
hexakis-(trans-4-tridecylcyclohexylcarbonyl)-scyllo-inositol
hexakis-(trans-4-tetradecylcyclohexylcarbonyl)-scyllo-inositol
hexakis-(trans-4-pentadecylcyclohexylcarbonyl)-scyllo-inositol
hexakis-(trans-4-hexadecylcyclohexylcarbonyl)-scyllo-inositol
hexakis-(trans-4-heptadecylcyclohexylcarbonyl)-scyllo-inositol
hexakis-(trans-4-octadecylcyclohexylcarbonyl)-scyllo-inositol
hexakis-(trans-4-nonadecylcyclohexylcarbonyl)-scyllo-inositol
hexakis-(trans-4-eicosylcyclohexylcarbonyl)-scyllo-inositol

EXAMPLE 2

A mixture of 1.8 g of scyllo-inositol, 70 mmol of for 2 hours. Customary working up (extraction with chloroform and flash column chromatography using 3:2 petroleum ether/chloroform) gives: hexakis-(p-n-nonylbenzoyl)-scyllo-inositol, m.p. 186°, c.p. 192°.

The following are obtained analogously using the corresponding acid chlorides:
hexakis-(p-methylbenzoyl)-scyllo-inositol
hexakis-(p-ethylbenzoyl)-scyllo-inositol
hexakis-(p-propylbenzoyl)-scyllo-inositol
hexakis-(p-butylbenzoyl)-scyllo-inositol
hexakis-(p-pentylbenzoyl)-scyllo-inositol
hexakis-(p-hexylbenzoyl)-scyllo-inositol
hexakis-(p-heptylbenzoyl)-scyllo-inositol, m.p. 221°–224°
hexakis-(p-octylbenzoyl)-scyllo-inositol, m.p. 198°–199.5°
hexakis-(p-nonylbenzoyl)-scyllo-inositol
hexakis-(p-decylbenzoyl)-scyllo-inositol
hexakis-(p-undecylbenzoyl)-scyllo-inositol
hexakis-(p-dodecylbenzoyl)-scyllo-inositol
hexakis-(p-tridecylbenzoyl)-scyllo-inositol
hexakis-(p-tetradecylbenzoyl)-scyllo-inositol
hexakis-(p-pentadecylbenzoyl)-scyllo-inositol
hexakis-(p-hexadecylbenzoyl)-scyllo-inositol
hexakis-(p-heptadecylbenzoyl)-scyllo-inositol
hexakis-(p-octadecylbenzoyl)-scyllo-inositol
hexakis-(p-nonadecylbenzoyl)-scyllo-inositol
hexakis-(p-eicosylbenzoyl)-scyllo-inositol
hexakis-(p-methoxybenzoyl)-scyllo-inositol
hexakis-(p-ethoxybenzoyl)-scyllo-inositol
hexakis-(p-propoxybenzoyl)-scyllo-inositol
hexakis-(p-butoxybenzoyl)-scyllo-inositol
hexakis-(p-pentoxybenzoyl)-scyllo-inositol
hexakis-(p-hexoxybenzoyl)-scyllo-inositol
hexakis-(p-heptyloxybenzoyl)-scyllo-inositol
hexakis-(p-octyloxybenzoyl)-scyllo-inositol, m.p. 230°–231°
hexakis-(p-nonyloxybenzoyl)-scyllo-inositol
hexakis-(p-decyloxybenzoyl)-scyllo-inositol, m.p. 210°–211°
hexakis-(p-undecyloxybenzoyl)-scyllo-inositol
hexakis-(p-dodecyloxybenzoyl)-scyllo-inositol
hexakis-(p-tridecyloxybenzoyl)-scyllo-inositol
hexakis-(p-tetradecyloxybenzoyl)-scyllo-inositol
hexakis-(p-pentadecyloxybenzoyl)-scyllo-inositol
hexakis-(p-hexadecyloxybenzoyl)-scyllo-inositol
hexakis-(p-heptadecyloxybenzoyl)-scyllo-inositol
hexakis-(p-octadecyloxybenzoyl)-scyllo-inositol
hexakis-(p-nonadecyloxybenzoyl)-scyllo-inositol
hexakis-(p-eicosyloxybenzoyl)-scyllo-inositol

EXAMPLE 3

3.48 g of scyllo-cyclohexane-1,2,3,4,5,6-hexacarboxylic acid is boiled for 1 hour with 14.4 g of $SOCl_2$, the mixture is evaporated, the resulting crude acid chloride is dissolved in 50 ml of toluene, and 5 ml of pyridine and 8.4 g of p-hydroxybenzonitrile are added and the mixture is boiled for 2 hours. Cooling and working up in the customary manner gives hexakis-(p-cyanophenyl)scyllo-cyclohexane-1,2,3,4,5,6-hexacarboxylate.

The following are obtained analogously by esterification:
hexakis-(p-methoxy-phenyl)scyllo-cyclohexane-1,2,3,4,5,6-hexacarboxylate
hexakis-(p-ethoxy-phenyl)scyllo-cyclohexane-1,2,3,4,5,6-hexacarboxylate
hexakis-(p-propoxy-phenyl)scyllo-cyclohexane-1,2,3,4,5,6-hexacarboxylate
hexakis-(p-butoxy-phenyl)scyllo-cyclohexane-1,2,3,4,5,6-hexacarboxylate
hexakis-(p-pentoxy-phenyl)scyllo-cyclohexane-1,2,3,4,5,6-hexacarboxylate
hexakis-(p-hexyloxy-phenyl)scyllo-cyclohexane-1,2,3,4,5,6-hexacarboxylate hexakis-(p-heptyloxy-phenyl)scyllo-cyclohexane-1,2,3,4,5,6-hexacarboxylate
hexakis-(p-octyloxy-phenyl)scyllo-cyclohexane-1,2,3,4,5,6-hexacarboxylate
hexakis-(p-nonyloxy-phenyl)scyllo-cyclohexane-1,2,3,4,5,6-hexacarboxylate
hexakis-(p-decyloxy-phenyl)scyllo-cyclohexane-1,2,3,4,5,6-hexacarboxylate
hexakis-(p-undecyloxy-phenyl)scyllo-cyclohexane-1,2,3,4,5,6-hexacarboxylate
hexakis-(p-dodecyloxy-phenyl)scyllo-cyclohexane-1,2,3,4,5,6-hexacarboxylate
hexakis-(p-tridecyloxy-phenyl)scyllo-cyclohexane-1,2,3,4,5,6-hexacarboxylate
hexakis-(p-tetradecyloxy-phenyl)scyllo-cyclohexane-1,2,3,4,5,6-hexacarboxylate
hexakis-(p-pentadecyloxy-phenyl)scyllo-cyclohexane-1,2,3,4,5,6-hexacarboxylate
hexakis-(p-methyl-phenyl)scyllo-cyclohexane-1,2,3,4,5,6-hexacarboxylate
hexakis-(p-ethyl-phenyl)scyllo-cyclohexane-1,2,3,4,5,6-hexacarboxylate
hexakis-(p-propyl-phenyl)scyllo-cyclohexane-1,2,3,4,5,6-hexacarboxylate
hexakis-(p-butyl-phenyl)scyllo-cyclohexane-1,2,3,4,5,6-hexacarboxylate
hexakis-(p-pentyl-phenyl)scyllo-cyclohexane-1,2,3,4,5,6-hexacarboxylate
hexakis-(p-hexyl-phenyl)scyllo-cyclohexane-1,2,3,4,5,6-hexacarboxylate
hexakis-(p-heptyl-phenyl)scyllo-cyclohexane-1,2,3,4,5,6-hexacarboxylate
hexakis-(p-octyl-phenyl)scyllo-cyclohexane-1,2,3,4,5,6-hexacarboxylate
hexakis-(p-nonyl-phenyl)scyllo-cyclohexane-1,2,3,4,5,6-hexacarboxylate
hexakis-(p-decyl-phenyl)scyllo-cyclohexane-1,2,3,4,5,6-hexacarboxylate
hexakis-(p-undecyl-phenyl)scyllo-cyclohexane-1,2,3,4,5,6-hexacarboxylate
hexakis-(p-dodecyl-phenyl)scyllo-cyclohexane-1,2,3,4,5,6-hexacarboxylate
hexakis-(p-tridecyl-phenyl)scyllo-cyclohexane-1,2,3,4,5,6-hexacarboxylate
hexakis-(p-tetradecyl-phenyl)scyllo-cyclohexane-1,2,3,4,5,6-hexacarboxylate
hexakis-(p-pentadecyl-phenyl)scyllo-cyclohexane-1,2,3,4,5,6-hexacarboxylate
hexakis-(p-methoxy-phenyl)mellitate
hexakis-(p-ethoxy-phenyl)mellitate
hexakis-(p-propoxy-phenyl)mellitate
hexakis-(p-butoxy-phenyl)mellitate
hexakis-(p-pentoxy-phenyl)mellitate
hexakis-(p-butoxy-phenyl)mellitate
hexakis-(p-pentoxy-phenyl)mellitate
hexakis-(p-hexoxy-phenyl)mellitate
hexakis-(p-heptyloxy-phenyl)mellitate
hexakis-(p-octyloxy-phenyl)mellitate
hexakis-(p-nonyloxy-phenyl)mellitate
hexakis-(p-decyloxy-phenyl)mellitate
hexakis-(p-undecyloxy-phenyl)mellitate
hexakis-(p-dodecyloxy-phenyl)mellitate
hexakis-(p-tridecyloxy-phenyl)mellitate
hexakis-(p-tetradecyloxy-phenyl)mellitate
hexakis-(p-pentadecyloxy-phenyl)mellitate
hexakis-(p-methyl-phenyl)mellitate
hexakis-(p-ethyl-phenyl)mellitate
hexakis-(p-propyl-phenyl)mellitate
hexakis-(p-butyl-phenyl)mellitate
hexakis-(p-pentyl-phenyl)mellitate
hexakis-(p-hexyl-phenyl)mellitate
hexakis-(p-heptyl-phenyl)mellitate
hexakis-(p-octyl-phenyl)mellitate
hexakis-(p-nonyl-phenyl)mellitate
hexakis-(p-decyl-phenyl)mellitate
hexakis-(p-undecyl-phenyl)mellitate
hexakis-(p-dodecyl-phenyl)mellitate
hexakis-(p-tridecyl-phenyl)mellitate
hexakis-(p-tetradecyl-phenyl)mellitate
hexakis-(p-pentadecyl-phenyl)mellitate

EXAMPLE 4

A mixture of 2.85 g of hexachlorobenzene, 17.5 g of trans-4-n-heptylcyclohexylmethylthiolate and 100 ml of HMPT is stirred at 20° under $N_2$ for 10 hours, evaporated and worked up in the customary manner to give hexakis-(trans-4-n-heptylcyclohexylmethylthio)-benzene.

The following are obtained analogously from hexachlorobenzene or β-hexachlorocyclohexane, respectively:
hexakis-(trans-4-butylcyclohexylmethylthio)-benzene
hexakis-(trans-4-pentylcyclohexylmethylthio)-benzene
hexakis-(trans-4-hexylcyclohexylmethylthio)-benzene
hexakis-(trans-4-octylcyclohexylmethylthio)-benzene
hexakis-(trans-4-nonylcyclohexylmethylthio)-benzene
hexakis-(trans-4-decylcyclohexylmethylthio)-benzene
hexakis-(trans-4-dodecylcyclohexylmethylthio)-benzene
scyllo-1,2,3,4,5,6-hexakis-(trans-4-butylcyclohexylmethylthio)-cyclohexane
scyllo-1,2,3,4,5,6-hexakis-(trans-4-pentylcyclohexylmethylthio)-cyclohexane
scyllo-1,2,3,4,5,6-hexakis-(trans-4-hexylcyclohexylmethylthio)-cyclohexane
scyllo-1,2,3,4,5,6-hexakis-(trans-4-octylcyclohexylmethylthio)-cyclohexane
scyllo-1,2,3,4,5,6-hexakis-(trans-4-nonylcyclohexylmethylthio)-cyclohexane
scyllo-1,2,3,4,5,6-hexakis-(trans-4-decylcyclohexylmethylthio)-cyclohexane
scyllo-1,2,3,4,5,6-hexakis-(trans-4-dodecylcyclohexylmethylthio)-cyclohexane

EXAMPLE 5

A mixture of 5 g of octakis-[2-(p-heptyloxycarbonylphenyl)-vinylene]-naphthalene [obtainable by heating a mixture of 7.6 g of octabromonaphthalene, 19.7 g of n-heptyl p-vinylbenzoate, 180 mg of palladium(II) acetate, 648 mg of triphenylphosphine, 8.08 g of triethylamine and 50 ml of dimethylformamide at 70° for 72 hours, filtering off the resulting triethylammonium hydrobromide after cooling, removing the solvent in vacuo and purifying the residue by chromatography over silica gel using toluene/ethyl acetate], 150 ml of dioxane and 4 g of Pd-on-charcoal (5%) is hydrogenated under normal pressure at 25° for 12 hours. Customary working up gives octakis-[2-(p-heptyloxycarbonylphenyl)-ethyl]-naphthalene.

The following are prepared analogously:
octakis-[2-(p-butoxycarbonylphenyl)-ethyl]-naphthalene
octakis-[2-(p-pentoxycarbonylphenyl)-ethyl]-naphthalene
octakis-[2-(p-hexoxycarbonylphenyl)-ethyl]-naphthalene octakis-[2-(p-octyloxycarbonylphenyl)-ethyl]-naphthalene
octakis-[2-(p-nonyloxycarbonylphenyl)-ethyl]-naphthalene
octakis-[2-(p-decyloxycarbonylphenyl)-ethyl]-naphthalene
octakis-[2-(p-undecyloxycarbonylphenyl)-ethyl]-naphthalene
octakis-[2-(p-dodecyloxycarbonylphenyl)-ethyl]-naphthalene
octakis-[2-(p-propoxyphenyl)-ethyl]-naphthalene
octakis-[2-(p-butoxyphenyl)-ethyl]-naphthalene
octakis-[2-(p-pentoxyphenyl)-ethyl]-naphthalene
octakis-[2-(p-hexoxyphenyl)-ethyl]-naphthalene
octakis-[2-(p-heptyloxyphenyl)-ethyl]-naphthalene
octakis-[2-(p-octyloxyphenyl)-ethyl]-naphthalene
octakis-[2-(p-nonyloxyphenyl)-ethyl]-naphthalene
octakis-[2-(p-decyloxyphenyl)-ethyl]-naphthalene
octakis-[2-(p-undecyloxyphenyl)-ethyl]-naphthalene
octakis-[2-(p-dodecyloxyphenyl)-ethyl]-naphthalene
octakis-[2-(p-butylphenyl)-ethyl]-naphthalene
octakis-[2-(p-pentylphenyl)-ethyl]-naphthalene
octakis-[2-(p-hexylphenyl)-ethyl]-naphthalene
octakis-[2-(p-heptylphenyl)-ethyl]-napthalene
octakis-[2-(p-octylphenyl)-ethyl]-naphthalene
octakis-[2-(p-nonylphenyl)-ethyl]-naphthalene
octakis-[2-(p-decylphenyl)-ethyl]-naphthalene
octakis-[2-(p-undecylphenyl)-ethyl]-naphthalene
octakis-[2-(p-dodecylphenyl)-ethyl]-naphthalene
octakis-[2-(p-cyanophenyl)-ethyl]-naphthalene
octakis-[2-(p-propoxybiphenyl-4-yl)-ethyl]-naohthalene
octakis-[2-(4'-butoxybiphenyl-4-yl)-ethyl]-naphthalene
octakis-[2-(4'-pentoxybiphenyl-4-yl)-ethyl]-naphthalene
octakis-[2-(4'-hexoxybiphenyl-4-yl)-ethyl]-naphthalene
octakis-[2-(4'-heptyloxybiphenyl-4-yl)-ethyl]-naphthalene
octakis-[2-(4'-octyloxybiphenyl-4-yl)-ethyl]-naphthalene
octakis-[2-(4'-nonyloxybiphenyl-4-yl)-ethyl]-naphthalene
octakis-[2-(4'-decyloxybiphenyl-4-yl)-ethyl]-naphthalene
octakis-[2-(4'-undecyloxybiphenyl-4-yl)-ethyl]-naphthalene
octakis-[2-(4'-dodecyloxybiphenyl-4-yl)-ethyl]-naphthalene
octakis-[2-(4'-butylbiphenyl-4-yl)-ethyl]-naphthalene
octakis-[2-(4'-pentylbiphenyl-4-yl)-ethyl]-naphthalene
octakis-[2-(4'-hexylbiphenyl-4-yl)-ethyl]-naphthalene
octakis-[2-(4'-heptylbiphenyl-4-yl)-ethyl]-naphthalene
octakis-[2-(4'-octylbiphenyl-4-yl)-ethyl]-naphthalene
octakis-[2-(4'-nonylbiphenyl-4-yl)-ethyl]-naphthalene
octakis-[2-(4'-decylbiphenyl-4-yl)-ethyl]-naphthalene
octakis-[2-(4'-undecylbiphenyl-4-yl)-ethyl]-naphthalene
octakis-[2-(4'-dodecylbiphenyl-4-yl)-ethyl]-naphthalene
octakis-[2-(4'-cyanobiphenyl-4-yl)-ethyl]-naphthalene

EXAMPLE 6

A mixture of 5 g of hexakis-[2-(p-nonyloxyphenyl)-vinylene]-benzene [obtainable by boiling a mixture of 5.52 g of hexabromobenzene, 14.76 g of p-nonyloxystyrene, 90 mg of palladium(II) acetate, 365 mg of tris-o-tolylphosphine, 6.06 g of triethylamine and 25 ml of acetonitrile for 72 hours, removing the solvent and purifying the residue by chromatography over silica gel using toluene/ethyl acetate], 100 ml of tetrahydrofuran and 3 g of Pd-on-charcoal (5%) is hydrogenated at 25° and normal pressure for 5 hours. Customary working up gives hexakis-[2-(p-nonloxyphenyl)-ethyl]-benzene.

The following are prepared analogously:
hexakis-[2-(p-methoxyphenyl)-ethyl]-benzene
hexakis-[2-(p-ethoxyphenyl)-ethyl]-benzene
hexakis-[2-(p-propoxyphenyl)-ethyl]-benzene
hexakis-[2-(p-butoxyphenyl)-ethyl]-benzene
hexakis-[2-(p-pentoxyphenyl)-ethyl]-benzene
hexakis-[2-(p-hexoxyphenyl)-ethyl]-benzene
hexakis-[2-(p-heptyloxyphenyl)-ethyl]-benzene
hexakis-[2-(p-octyloxyphenyl)-ethyl]-benzene
hexakis-[2-(p-decyloxyphenyl)-ethyl]-benzene
hexakis-[2-(p-undecyloxyphenyl)-ethyl]-benzene
hexakis-[2-(p-dodecyloxyphenyl)-ethyl]-benzene
hexakis-[2-(p-tridecyloxyphenyl)-ethyl]-benzene
hexakis-[2-(p-tetradecyloxyphenyl)-ethyl]-benzene
hexakis-[2-(p-pentadecyloxyphenyl)-ethyl]-benzene
hexakis-[2-(p-hexadecyloxyphenyl)-ethyl]-benzene
hexakis-[2-(p-heptadecyloxyphenyl)-ethyl]-benzene
hexakis-[2-(p-octadecyloxyphenyl)-ethyl]-benzene
hexakis-[2-(p-nonadecyloxyphenyl)-ethyl]-benzene
hexakis-[2-(p-eicosyloxyphenyl)-ethyl]-benzene
hexakis-[2-(p-methylphenyl)-ethyl]-benzene
hexakis-[2-(p-ethylphenyl)-ethyl]-benzene
hexakis-[2-(p-propylphenyl)-ethyl]-benzene
hexakis-[2-(p-butylphenyl)-ethyl]-benzene
hexakis-[2-(p-pentylphenyl)-ethyl]-benzene
hexakis-[2-(p-hexylphenyl)-ethyl]-benzene
hexakis-[2-(p-heptylphenyl)-ethyl]-benzene
hexakis-[2-(p-octylphenyl)-ethyl]-benzene
hexakis-[2-(p-nonylphenyl)-ethyl]-benzene
hexakis-[2-(p-decylphenyl)-ethyl]-benzene
hexakis-[2-(p-undecylphenyl)-ethyl]-benzene
hexakis-[2-(p-dodecylphenyl)-ethyl]-benzene
hexakis-[2-(p-tridecylphenyl)-ethyl]-benzene
hexakis-[2-(p-tetradecylphenyl)-ethyl]-benzene
hexakis-[2-(pentadecylphenyl)-ethyl]-benzene
hexakis-[2-(hexadecylphenyl)-ethyl]-benzene
hexakis-[2-(heptadecylphenyl)-ethyl]-benzene
hexakis-[2-(p-octadecylphenyl)-ethyl]-benzene
hexakis-[2-(p-nonadecylphenyl)-ethyl]-benzene
hexakis-[2-(p-eicosylphenyl)-ethyl]-benzene

EXAMPLE 7

A mixture of 2 g of hexakis-[2-(p-cyanophenyl)-vinylene]-benzene [obtainable by boiling a mixture of 5.52 g of hexabromobenzene, 7.74 g of 4-vinylbenzonitrile, 120 mg of NiCl$_2$(PPh$_3$)$_2$(NiCl$_2$(Ph)$_2$—P—CH$_2$C-H$_2$—P—(Ph)$_2$ is also suitable as a catalyst), 365 mg of tris-o-tolylphosphine, 6.06 g of triethylamine and 50 ml of tetrahydrofuran for 72 hours, removing the solvent and purifying the residue by chromatography over silica gel using methylene chloride/methanol], 50 ml of ethanol and 1 g of Pd-on-charcoal (5%) is hydrogenated at 25° and normal pressure for 10 hours. Customary working up gives hexakis-[2-(p-cyanophenyl)-ethyl]-benzene.

The following are prepared analogously:
hexakis-[2-(4'-cyanobiphenyl-4-yl)-ethyl]-benzene
hexakis-[2-(p-(trans-4-heptylcyclohexyl)-phenyl)-ethyl]-benzene
hexakis-[2-(p-(trans-4-octylcyclohexyl)-phenyl)-ethyl]-benzene
hexakis-[2-(p-(trans-4-nonylcyclohexyl)-phenyl)-ethyl]-benzene
hexakis-[2-(p-(trans-4-decylcyclohexyl)-phenyl)-ethyl]-benzene hexakis-[2-(p-(trans-4-undecylcyclohexyl)-phenyl)-ethyl]-benzene
hexakis-[2-(p-(trans-4-dodecylcyclohexyl)-phenyl)-ethyl]-benzene

EXAMPLE 8

A mixture of 2 g of hexakis-[2-(4-pyridyl)-vinylene]-benzene [obtainable by boiling a mixture of 5.52 g of hexabromobenzene, 6.3 g of 4-vinylpyridine, 90 mg of palladium(II) acetate, 365 mg of tris-o-tolyphosphine, 6.06 g of triethylamine and 50 ml of acetonitrile for 48 hours, removing the solvent and purifying the residue by chromatography over silica gel using toluene/ethyl acetate], 50 ml of ethanol and 1 g of Pd-on-charcoal (5%) is hydrogenated at 25° and normal pressure for 10 hours.

Customary working up gives hexakis-[2-(4-pyridyl)-ethyl]-benzene.

The following are prepared analogously:
hexakis-[2-(3-pyridyl)-ethyl]-benzene
hexakis-[2-(2-pyridyl)-ethyl]-benzene
hexakis-[2-(2-pyrimidinyl)-ethyl]-benzene
hexakis-[2-(5-pyrimidinyl)-ethyl]-benzene

EXAMPLE 9

A mixture of 17.4 g of hexahydroxybenzene, 260 g of trans-4-n-nonyl-1-iodomethylcyclohexane, 41.4 g of $K_2CO_3$ and 350 ml of DMF is heated at 80° for 16 hours, with stirring, and is then cooled and worked up in the customary manner. This gives hexakis-[(trans-4-n-nonylcyclohexyl)-methoxy]-benzene.

The following are prepared analogously:
hexakis-[(trans-4-heptylcyclohexyl)-methoxy]-benzene
hexakis-[(trans-4-octylcyclohexyl)-methoxy]-benzene
hexakis-[(trans-4-decylcyclohexyl)-methoxy]-benzene
hexakis-[(trans-4-undecylcyclohexyl)-methoxy]-benzene
hexakis-[(trans-4-dodecylcyclohexyl)-methoxy]-benzene
hexakis-[(trans-4-heptylcyclohexyl)-methylthio]-benzene
hexakis-[(trans-4-octylcyclohexyl)-methylthio]-benzene
hexakis-[(trans-4-decylcyclohexyl)-methylthio]-benzene
hexakis-[(trans-4-undecylcyclohexyl)-methylthio]-benzene
hexakis-[(trans-4-dodecylcyclohexyl)-methylthio]-benzene
hexakis-[(trans-4-(trans-4-heptylcyclohexylcarbonyloxy)cyclohexyl)-methoxy]-benzene
hexakis-[(trans-4-(trans-4-octylcyclohexylcarbonyloxy)cyclohexyl)-methoxy]-benzene
hexakis-[(trans-4-(trans-4-decylcyclohexylcarbonyloxy)cyclohexyl) -methoxy]-benzene
hexakis-[(trans-4-(trans-4-undecylcyclohexylcarbonyloxy)cyclohexyl)-methoxy]-benzene
hexakis-[(trans-4-(trans-4-dodecylcyclohexylcarbonyloxy)cyclohexyl)-methoxy]-benzene The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a discotic liquid crystalline phase comprising at least two liquid crystalline components, the improvement wherein at least one of said components is a carbocyclic compound of the formula 1a, 1b or 1c

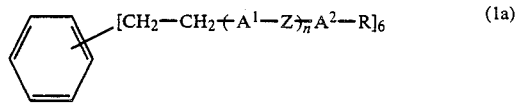

(1a)

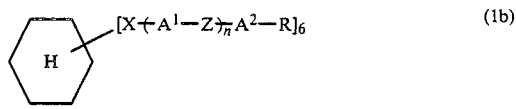

(1b)

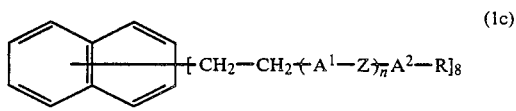

(1c)

wherein
X is —$CH_2$—$(CH_2)_p$— or —$CH_2$—$(CH_2)_p$— wherein one or two non-adjacent $CH_2$ groups are replaced by —O—, —S—, —CO—, —O—CO—, —CO—O— or —CH=CH,
p is 0, 1 or 2,
$A^1$ and $A^2$ independently are each 1,4-phenylene or 1,4-phenylene substituted by halogen, $CH_3$ or CN; 1,4-phenylene or 1,4-phenylene substituted by halogen, $CH_3$ or CN wherein one or more CH groups are replaced by N atoms; 1,4-cyclohexylene, 1,4-cyclohexylene substituted in the 1-position or 4-position by CN, or 1,4-cyclohexylene wherein one or two non-adjacent $CH_2$ groups are replaced by —O— or —S—; piperidine-1,4-diyl; or 1,4-bicyclo[2.2.2]octylene,
Z is —CO—O—, —O—CO—, —O—, —$CH_2$—, —$CH_2O$—, —$OCH_2$—, —$CH_2CH_2$, —CHCN—$CH_2$—, —$CH_2$—CHCN—, —CH=CH—, —CH=N—, —N=CH—, —NO=N—, —N=NO— or a single bond,
n is 0, 1 or 2 and
R is alkyl of 1 to 20 C atoms or alkyl having 1–20 carbon atoms wherein one or more nonadjacent $CH_2$ groups are replaced by —O—, —CO—, —O—CO—, —CO—O— or —CH=CH—, H, F, Cl, Br, I, OH, $NH_2$, COOH or CN.

2. A phase of claim 1, wherein the carbocyclic compound has the formula

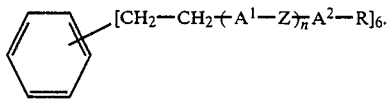

3. A phase of claim 1, wherein the carbocyclic compound has the formula

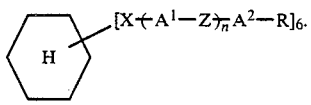

4. A phase of claim 1, wherein the carbocyclic compound has the formula

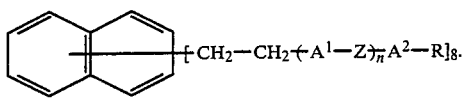

5. A phase of claim 1, wherein said compound is of the formula

Ch[—O—CO—($A^1$—Z)$_n$—$A^2$—R]$_6$

Ch[—CO—O—($A^1$—Z)$_n$—$A^2$—R]$_6$

Ch[—O—CH$_2$—($A^1$—Z)$_n$—$A^2$R]$_6$

Ch[—CH$_2$—O—($A^1$—Z)$_n$—$A^2$—R]$_6$

Ch[—CH$_2$CH$_2$—($A^1$—Z)$_n$—$A^2$—R]$_6$

Ch[—OCH$_2$CH$_2$—($A^1$—Z)$_n$—$A^2$—R]$_6$

Ch[—CH$_2$CH$_2$CH$_2$—($A^1$—Z)$_n$—$A^2$—R]

Ch[—SCH$_2$—($A^1$—Z)$_n$—$A^2$—R]$_6$

Bz[—CH$_2$CH$_2$—($A^1$—Z)$_n$—$A^2$—R]$_6$

Np[—CH$_2$CH$_2$—($A^1$—Z)$_n$—$A^2$—R]$_8$ where Ch is

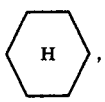

Bz is

and Np is

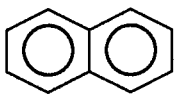

6. A phase of claim 3, wherein the substituents opposite each other are situated equatorially and in the trans-position.

7. A phase of claim 5, wherein said compound is of the formula

Ch[—O—CO—($A^1$—Z)$_n$—$A^2$—R]$_6$

Ch[—CO—O—($A^1$—Z)$_n$—$A^2$—R]$_6$

Ch[—O—CH$_2$—($A^1$—Z)$_n$—$A^2$R]$_6$

Ch[—CH$_2$CH$_2$—($A^1$—Z)$_n$—$A^2$—R]$_6$

Ch[—OCH$_2$CH$_2$—($A^1$—Z)$_n$—$A^2$—R]$_6$.

8. A phase of claim 1, wherein $A^1$ and $A^2$ are independently 1,4-cyclohexylene (Cy), 1,4-phenylene (Phe), 1,3-dioxane (Dio), 1,3-dithiane-2,5-diyl (Dit), bicyclo[2.2.2]octylene, piperidine-1,4-diyl (Dip), pyridyl (Pyn), pyrimidine (Pyr), 1,4-phenylene 2-substituted by F, Cl, CN or CH$_3$ or 1,4-phenylene 3-substituted by F, Cl, CN or CH$_3$.

9. A phase of claim 8, wherein $A^1$ and $A^2$ are independently Cy, Phe or Pyn.

10. A phase according to claim 1, wherein $A^1$ and $A^2$ are independently trans-1,4-cyclohexylene, trans-1,4-cyclohexylene 1-substituted in an axial position by CN or trans-1,4-cyclohexylene 4-substituted in an axial position by CN.

11. A phase according to claim 10, wherein n is 0 or 1.

12. A phase according to claim 11, wherein Z is —CO—O—, —O—CO—, —CH$_2$O—, —OCH$_2$—, —CH$_2$CH$_2$— or a single bond.

13. A phase according to claim 1, wherein —($A^1$—Z)$_n$—$A^2$— is

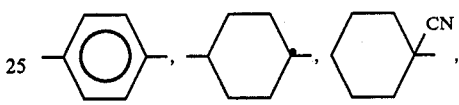

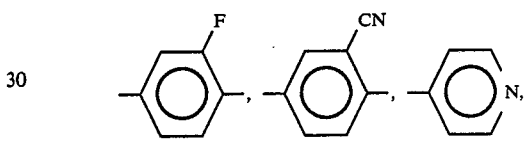

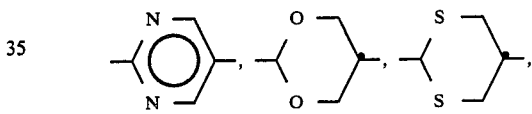

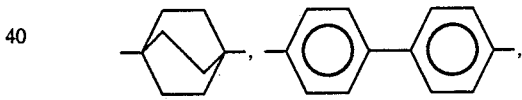

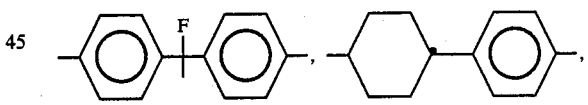

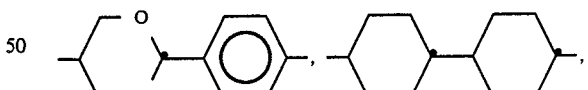

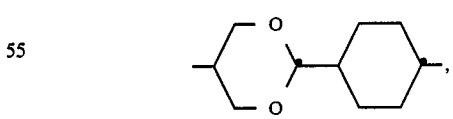

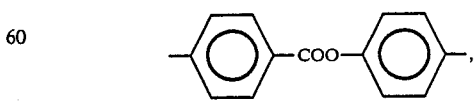

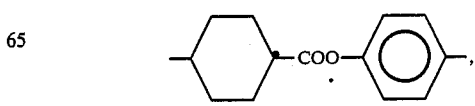

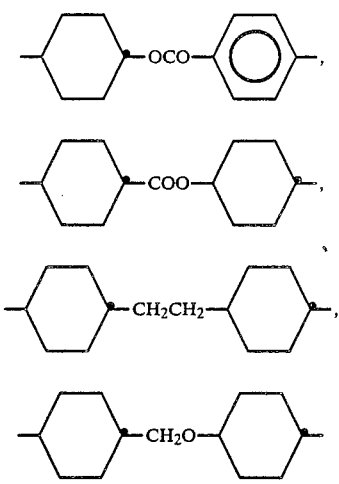

14. A phase according to claim 8, wherein R is —Oalkyl, —CO—O—alkyl, —O—CO—alkyl, —CO—alkyl, —CH₂—CH=CH—alkyl(trans), —CH₂CH₂—CH=CH—alkyl(trans), F, OH, COOH, CN or alkyl in which a non-terminal CH₂ group or two non-adjacent CH₂ groups are replaced by O atoms.

15. A phase according to claim 8, wherein R is propyl, butyl, pentyl, hexyl, heptyl, octyl, nonyl, decyl, undecyl, dodecyl, tridecyl, 2-oxapropyl, 2-oxabutyl, 3-oxabutyl, 2-oxapentyl, 3-oxapentyl, 4-oxapentyl, 2-oxahexyl, 3-oxahexyl, 4-oxahexyl, 5-oxahexyl, 2-oxaheptyl, 3-oxaheptyl, 4-oxaheptyl, 5-oxaheptyl, 6-oxaheptyl, ethyl, tetradecyl, pentadecyl, 2-oxaoctyl, 3-oxaoctyl, 4-oxaoctyl, 5-oxaoctyl, 6-oxaoctyl, 7-oxaoctyl, 2-oxanonyl, 3-oxanonyl, 4-oxanonyl, 5-oxanonyl, 6-oxanonyl, 7-oxanonyl, 8-oxanonyl, 2-oxadecyl, 3-oxadecyl, 4-oxadecyl, 5-oxadecyl, 6-oxadecyl, 7-oxadecyl, 8-oxadecyl, 9-oxadecyl, 2-oxaundecyl, 3-oxaundecyl, 4-oxaundecyl, 5-oxaundecyl, 6-oxaundecyl, 7-oxaundecyl, 8-oxaundecyl, 9-oxaundecyl, 10-oxaundecyl, 2-oxatridecyl, 2-oxatridecyl, 3-oxatridecyl, 4-oxatridecyl, 5-oxatridecyl, 6-oxatridecyl, 7-oxatridecyl, 8-oxatridecyl, 9-oxatridecyl, 10-oxatridecyl, 11-oxatridecyl, 12-oxatridecyl, 2,4-dioxapentyl, 2,4-dioxahexyl, 2,5-dioxahexyl, 3,5-dioxahexyl, 2,4-dioxaheptyl, 2,5-dioxaheptyl, 2,6-dioxaheptyl, 3,5-dioxaheptyl, 3,6-dioxaheptyl or 4,6-dioxaheptyl.

16. A phase according to claim 8, wherein R is isopropyl, 2-butyl, isobutyl, 2-methylbutyl, isopentyl, 2-methylpentyl, 3-methylpentyl, 2-ethylhexyl, 2-propylpentyl, 2-oxa-3-methylbutyl or 3-oxa-4-methylpentyl.

17. A phase of claim 1, wherein X is —O—CO—, —O—CH₂— —O—CH₂CH₂—, —CH₂—CH₂—, —CH₂—CH₂—CH₂—, —CO—O— or —CH₂—O—, and p is 0 or 1.

18. In a display element, based on a liquid crystal phase, the improvement wherein the phase is one of claim 1.

19. In an electrooptical display element based on a liquid crystalline dielectric, the improvement wherein the dielectric is a phase of claim 1.

* * * * *